United States Patent [19]
Rona et al.

[11] Patent Number: 5,947,370
[45] Date of Patent: Sep. 7, 1999

[54] APPARATUS AND METHOD FOR REAL TIME BOILING POINT DETECTION AND CONTROL

[75] Inventors: Mehmet Rona, Cambridge; Douglas J. Ely, North Andover; William E. Morgan, Carlisle, all of Mass.; Steven S. Carroll, deceased, late of Kent, Conn., by Richard P. Carroll, Executor

[73] Assignee: Arthur D. Little, Inc., Cambridge, Mass.

[21] Appl. No.: 09/079,573

[22] Filed: May 15, 1998

Related U.S. Application Data

[63] Continuation of application No. PCT/US96/18752, Nov. 22, 1996
[60] Provisional application No. 60/007,486, Nov. 22, 1995.
[51] Int. Cl.⁶ .............................. F23N 1/08; G01N 25/02
[52] U.S. Cl. ..................... 236/20 A; 236/78 D; 374/27; 374/107
[58] Field of Search ................................ 236/20 A, 78 D; 126/39; 219/516; 374/27, 107

[56] References Cited

U.S. PATENT DOCUMENTS

| | | | |
|---|---|---|---|
| 4,492,336 | 1/1985 | Takata et al. ........................ | 236/20 A |
| 4,549,527 | 10/1985 | Davis ..................................... | 126/374 |
| 4,646,963 | 3/1987 | Delotto et al. ........................ | 236/20 A |
| 4,781,469 | 11/1988 | Turon-Lagot .......................... | 374/27 |
| 4,858,119 | 8/1989 | Waugh et al. ........................ | 364/400 |
| 5,244,379 | 9/1993 | Stirling et al. ....................... | 431/6 |
| 5,310,110 | 5/1994 | Alamatsu et al. ..................... | 236/20 A |
| 5,451,746 | 9/1995 | Kadwel et al. ........................ | 219/506 |
| 5,540,215 | 7/1996 | Fritzsche et al. ..................... | 126/374 |
| 5,639,023 | 6/1997 | Hild et al. ............................. | 236/20 A |

OTHER PUBLICATIONS

"Gas Research institute", An advanced gas cooktop with The Simmer Sentry—an innovation in cooking convenience, pp. 1–2.
"Caloric Corporation", Servicing Instructions Caloric "Thermo–set" Burner and Convertible Griddle Burner with Flame Set, pp. 1–2.
"New Stanton Division Robertshaw—Controls Company", Robertshaw Gas Thermal Eye . . . with Flame Set, Lighting Instructions, pp. 1–3.
"Caloric Corporation", Caloric Compacto Gas Range Owners Guide, pp. 1–3.

Primary Examiner—William Wayner
Attorney, Agent, or Firm—Pearson & Pearson

[57] ABSTRACT

A system for monitoring and controlling the state of a thermal process. The system applies a modulated heat input to a liquid in a vessel and a thermal response measured at the bottom of the vessel provides information for real time processing of thermal properties of the liquid as it is being heated. Detection and control of an unknown boiling point enables a steady simmer or boiling condition in the liquid to be maintained.

57 Claims, 9 Drawing Sheets

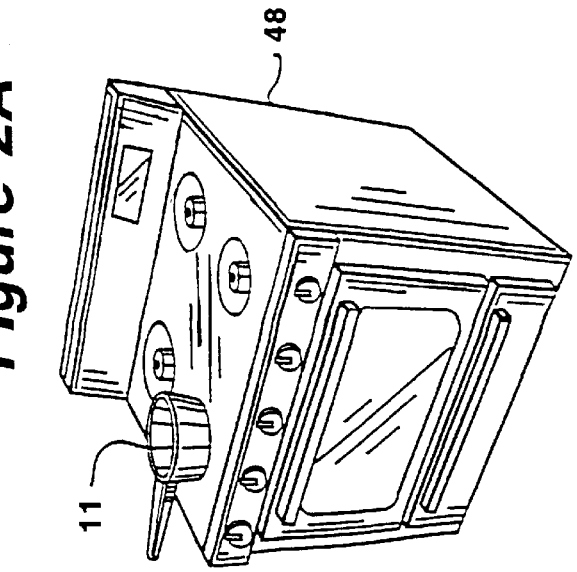
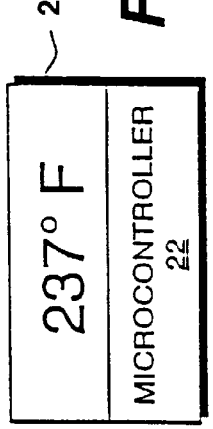
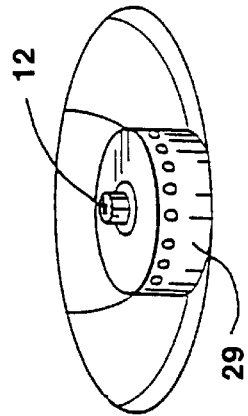
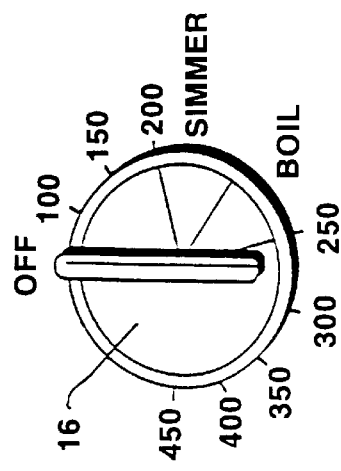
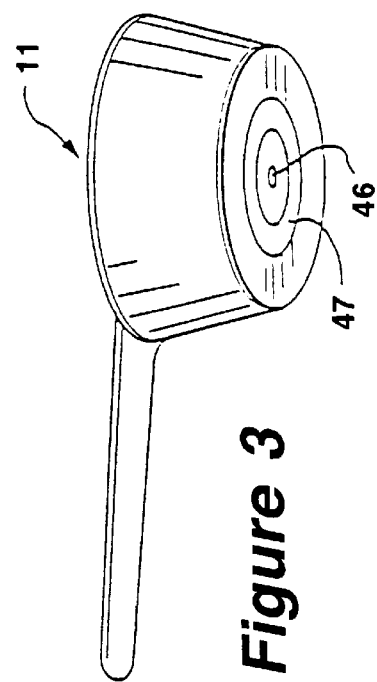

APPARATUS AND METHOD FOR REAL TIME BOILING POINT DETECTION AND CONTROL

This is a Continuation Application of International Application Serial No. PCT/US96/18752, filed Nov. 22, 1996, which is claiming priority of U.S. Provisional Application Serial No. 60/007,486, filed Nov. 22, 1995.

BACKGROUND OF THE INVENTION

1. Field of the Invention

This invention generally relates to monitoring and controlling the state of a thermal process and in particular to the real time detection and control of a thermal state of a liquid in a vessel at or below its boiling point on a gas cooktop burner by applying a modulated heat input and measuring and processing the thermal dynamic response that results.

2. Description of Related Art

Many processes for industrial, commercial, and residential applications involve the supplying of energy into an often inhomogeneous media. In some examples such as cooking, such a process might even give rise to chemical changes. The process involves radiation, convection, and phase transformation, and often is chaotic. Thus, to perform a simple temperature control is untenable. Even the most common situations such as simple boiling of water are chaotic and therefore extremely complicated. In the past, numerous attempts to keep track of the cooking process by means of various sensors have not been successful. A common user requirement is to maintain a steady simmer or boiling condition in a liquid. A controller which provides only temperature regulation cannot reliably meet this requirement because its setpoint temperature must be set to closely match the boiling point of the particular liquid, e.g. it must account for a temperature drop across the vessel wall, amount of salt present and altitude above sea level. If the commanded temperature is not accurately set, a temperature regulator will either fail to bring about the desired simmer/boil state or will continuously overheat the subject by trying to reach a temperature above the boiling point of the liquid contents.

Two prior art attempts to construct a smart cooktop have met with only limited success. The first attempt used a capillary-type thermostatic valve with a spring loaded sensor at the center of the burner to control temperature of the pot surface; it is described in a field service publication for a Model FA-C combination gas-cock and thermostat published in 1965 by Robertshaw-Controls Co., of Youngwood, Pa. USA which was used in a gas range Model 73YXT manufactured by Caloric Corporation of Topton, Pa. USA. Some versions incorporated an adjustment to control maximum flame size. This system was fairly good at temperature control; however, it was not sufficiently accurate to hold a low boil nor could it detect changes in the boiling point or a boil dry condition. The second attempt described in a 1995 brochure "Simmer Sentry" of the Gas Research Institute of Chicago, Illinois USA, was more sophisticated, incorporating both acoustic and temperature sensors in a "wand" that was plugged into the range control panel and immersed in the pot. The intrusive nature of the "wand" was inconvenient, and the performance was less than desired.

In U.S. Pat. No. 4,646,913, issued to Romeo Delotto et al., on Mar. 3, 1987, and assigned to Indesit Industria Electtrodomestici Italiana S.P.A., a sensor group is described for automatic temperature control for foods in vessels heated by a flame from a gas burner that contacts the vessels' bottom. The burner includes a vertical nozzle and the nozzle axis and sensing group are both off center with respect to the burner axis. Foods in the vessels are progressively heated and their temperature is sensed by a first sensor which when boiling occurs remains constant. A second sensor, which controls a gas supply line, senses increasing temperature slightly but continuously and limits the gas supply. Because this approach is dependent upon progressive heating of the vessel's contents, it would not be suitable where substances are added to the vessel contents or where stirring of the vessel contents replaces hot fluid with cold fluid near the sensor.

SUMMARY OF THE INVENTION

Therefore it is an object of this invention to provide automatic control of liquid heating processes by regulated heating of an unknown liquid to a temperature related to its boiling point using only a temperature measurement and without prior knowledge of the boiling point temperature of the liquid.

It is another object of the invention to sense imminent boiling in order to control a simmer or a rolling boil.

It is a further object of the invention to provide a mode of operation to control temperature in order to prevent burning, boil dry, boilovers and overcooking.

It is another object of this invention to provide a mode of operation whereby a temperature is selected at a vessel and heat is applied to maintain the selected temperature at the vessel.

It is yet another object of this invention to perform process control by seeing through noise caused by chaotic processes.

It is still another object of this invention to provide autonomous control of the cooking process atop a gas appliance.

It is another object of this invention to provide a method of process control which relies on modulating or pulsing an input and learning about the system in real time using phase sensitive detection of the system's response to the varying input.

The objects are further accomplished by providing in a system for monitoring and controlling the state of a thermal process, the improvement comprising means for providing a fluctuating heat input to the container in response to a heat control signal, means in contact with the container for sensing temperature, means connected to the temperature sensing means for calculating parameters based on fluctuations of temperature at the container, the parameters including an average linear rate of change ($\alpha$) of the temperature, an amplitude ($\beta$) of the temperature fluctuations in response to the fluctuating heat input, and a phase shift ($\phi$) of the temperature fluctuations relative to the fluctuating heat input, fuzzy logic means having inputs connected to the $\alpha$, $\beta$, and $\phi$ outputs of the parameter calculating means and the heat control signal for generating a signal indicating a boiling point of the liquid, and means connected to an output of the fuzzy logic means for generating the heat control signal. The container comprises a metal and the metal comprises aluminum, copper, steel, stainless steel, cast iron or combinations thereof. The temperature sensing means comprises a resistance temperature device (RTD), a thermocouple or an infrared sensor. The calculating parameter means comprises solving a time-temperature equation $T(t) = \alpha t + \beta \sin(\omega t + \phi)$.

The objects are further accomplished by providing in a cooking appliance for heating a liquid in a vessel, the improvement comprising means for setting a mode of operation for detecting and controlling a boiling point of the liquid, means for providing a heat input to the vessel in response to a heat control signal, the heat input including a fluctuating heat input, means positioned within the heat input providing means and in contact with the vessel for sensing temperature, means connected to the temperature sensing means for calculating parameters based on fluctuations of temperature at the vessel, the parameters including a linear rate of change ($\alpha$) of the temperature, an amplitude ($\beta$) of the temperature fluctuations in response to the fluctuating heat input, and a phase shift ($\phi$) of the temperature fluctuations relative to the fluctuating heat input, fuzzy logic means, having inputs connected to the $\alpha$, $\beta$, and $\phi$ outputs of the parameter calculating means and the heat control signal, for generating a signal indicating a boiling point of the liquid, means connected to an output of the fuzzy logic means for generating the heat control signal, the heat control signal maintaining the liquid temperature in accordance with the preset mode of operation, and means coupled to the temperature sensing means for supervising the mode of operation including the calculating parameter means, the fuzzy logic means and the proportional/integral/derivative means. The heating input providing means comprises a gas burner. The appliance comprises a plurality of heat input providing means, each of the heat input providing means being controlled in accordance with a preselected mode of operation. The vessel comprises a metal, and the metal comprises aluminum, copper, steel, stainless steel, cast iron or combinations thereof. The calculating parameter means comprises solving a time-temperature equation $T(t)=\alpha t + \beta \sin(\omega t + \phi)$. The appliance comprises a display means coupled to the supervising means for displaying information.

The objects are further accomplished by providing in a method for monitoring and controlling the state of a thermal process in a container holding a liquid, an improvement comprising the steps of providing a fluctuating heat input to the container in response to a heat control signal, sensing temperature with means in contact with the container, calculating parameters based on fluctuations of temperature at the container provided by the temperature sensing means, the parameters including a linear rate of change ($\alpha$) of the temperature, an amplitude ($\beta$) of the temperature fluctuations in response to the fluctuating heat input, and a phase shift ($\phi$) of the temperature fluctuations relative to the fluctuating heat input, generating a signal indicating a boiling point of the liquid with fuzzy logic means, having inputs connected to the $\alpha$, $\beta$, and $\phi$ outputs of the parameter calculating means and the heat control signal for controlling the fluctuating heat input providing means, and generating the heat control signal with means connected to an output of the fuzzy logic means. The method includes the step of providing the container comprising a metal, and the metal comprises aluminum, copper, steel, stainless steel, cast iron or combinations thereof. The step of calculating parameters comprises the step of solving a time-temperature equation $T(t)=\alpha t + \beta \sin(\omega t + \phi)$. The step of generating a signal indicating a boiling point of the liquid with fuzzy logic means comprises the step of preconditioning logic rules of the fuzzy logic means with empirical boiling point data for a plurality of types of liquids and containers prior to the fuzzy logic means being used in the system for detecting the boiling point. The step of generating the heat control signal comprises the steps of providing a proportional/integral/derivative means connected to an output of the fuzzy logic means for generating a response based on detecting the boiling point, and generating the heat control signal with heat control means connected to the response of the proportional/integral/derivative means.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIGS. 2A–2D are pictorial views of a gas cooking appliance including exploded views of components of the invention and showing a cooking vessel on top of a burner;

FIG. 3 is a pictorial view of the cooking vessel in FIG. 2 showing a bottom center point where temperature is measured and illustrating a circular zone around the center point where a gas flame applies heat;

DESCRIPTION OF ILLUSTRATIVE EMBODIMENT

Figure 1:
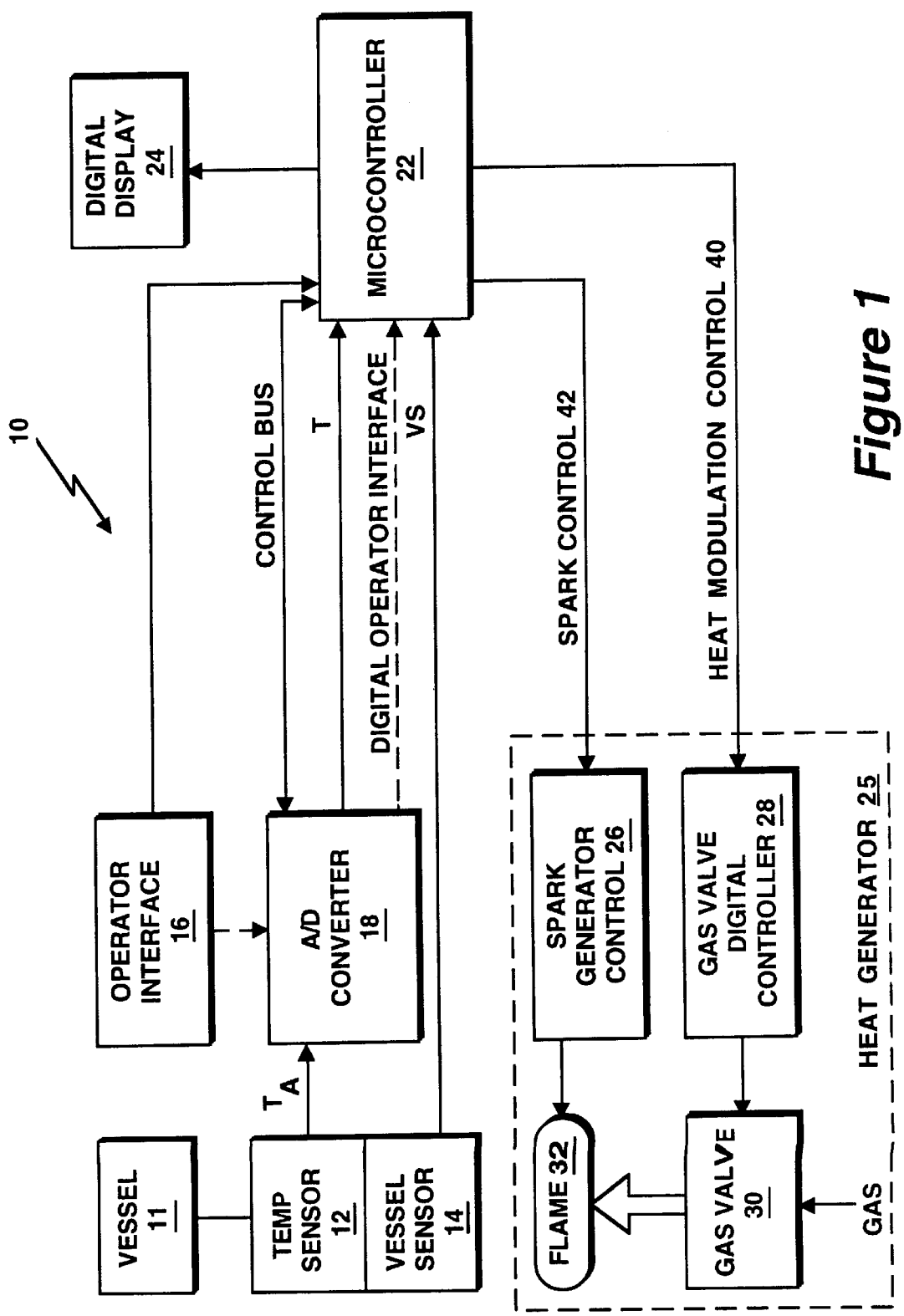
FIG. 1 is a block diagram of the invention for real time detecting and controlling of the boiling point of a liquid in a vessel.
Figure 4:
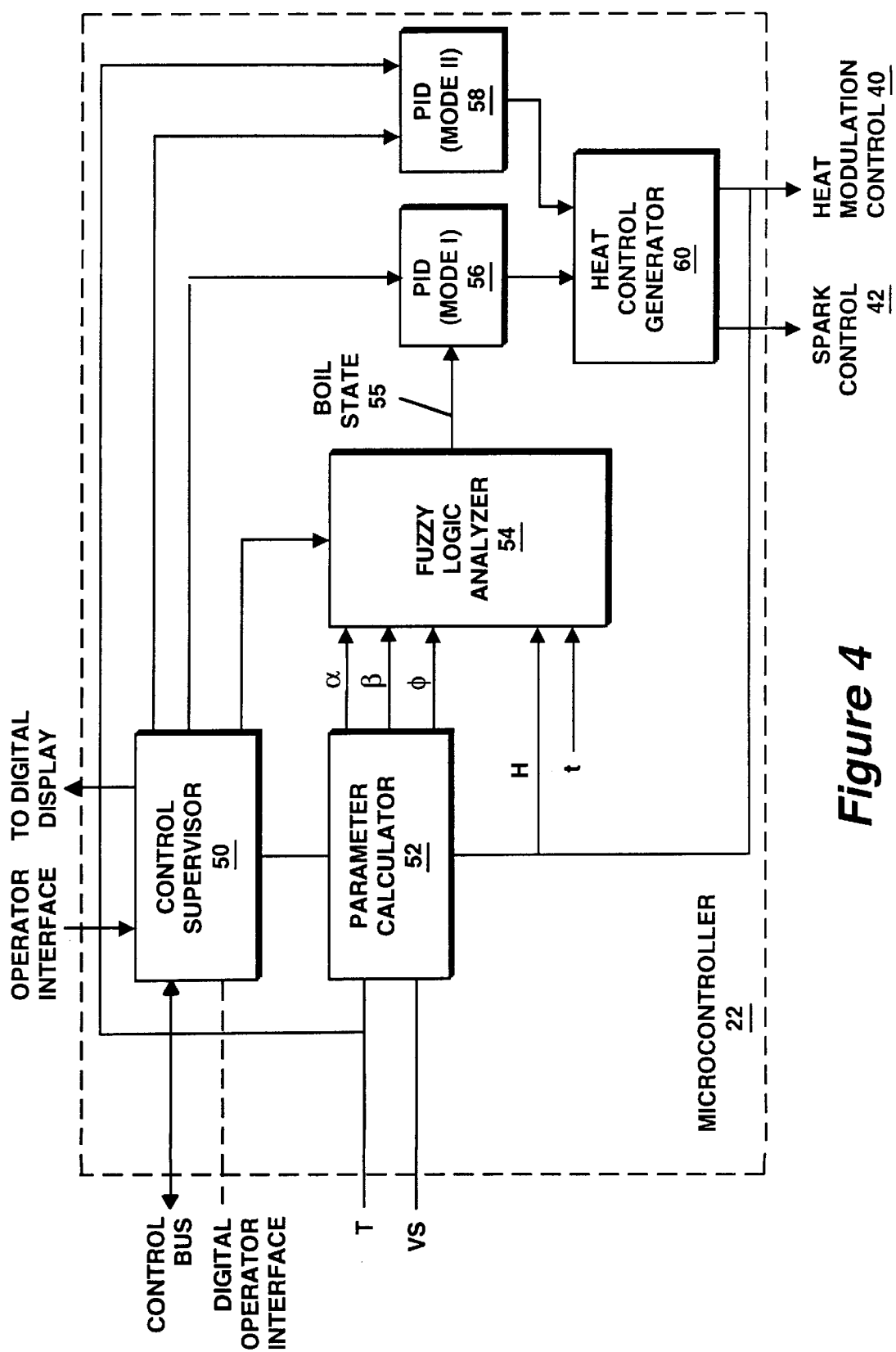
FIG. 4 is a block diagram of functions performed in the microcontroller of FIG. 1.

Referring to FIG. 1 and FIG. 4, block diagrams are shown of the invention for monitoring and controlling the state of a thermal process. The process control relies on modulating or pulsing an input and then learning about the system in real time using phase sensitive detection of the system's response to the varying input. This method is particularly applicable to controlling the energy input or gas flow of gas cooktop burners. The block diagram of FIG. 1 comprises a system 10 for the real time detecting and controlling of a known or unknown boiling point of a liquid in a vessel 11. FIG. 4 is a block diagram of the functions performed by the microcontroller 22 of FIG. 1.

Referring again to FIG. 1, the system 10 comprises a container or vessel 11 for holding a liquid which is positioned on a frame of a burner 29 (FIG. 2C) having a spring loaded temperature sensor 12 for measuring the temperature of the bottom of the vessel 11. The term liquid used herein includes liquids comprising non-liquid elements such as solids and semi-solids. A container or vessel sensor 14 is also provided on the frame of the burner for signaling the presence of the vessel 11. The vessel 11 is heated by a heat generator 25 comprising a gas flame 32 and the gas is provided via a gas valve 30. The temperature sensor 12 comprises a spring loaded resistance temperature device (RTD) which is shielded from the convective and radiative perturbation of the gas flame 32 by means of a cup. The temperature signal ($T_A$) is fed to an analog to digital (A/D) converter 18 and the digital output T of the A/D converter 18 is fed to the microcontroller 22. A control bus is connected between, the A/D converter 18 and the microcontroller 22. The microcontroller 22 analyzes the temperature data in accordance with modulated heat inputs from the heat generator 25 applied to the vessel 11 and the liquid therein and calculates the parameters which provide the boiling point data for the liquid in the container vessel 11. The heat generator 25 also comprises a spark generator control 26 for igniting the gas and a gas valve digital controller 28 for controlling the gas valve 30. A gas valve analog controller may also be employed. The microcontroller 22 generates a heat modulation control 40 signal and a spark 42 signal. It also provides information to a digital display 24 for displaying information about the thermal or cooling process. The heat modulation control 40 signal is fed to the gas valve digital controller 28 which regulates the gas valve 30 thereby providing varying amounts of gas to the flame 32 which produces the modulated heat input to the vessel 11 and liquid therein. A digital output signal from an operator interface 16, which comprises a control knob 16 set by an operator, is fed to the microcontroller 22 and optionally to the A/D converter 18, when the signal is analog, and the A/D converter 18 generates a digital signal (digital operator interface) for the microcontroller 22 to process. The real time control system 10 senses imminent boiling and controls anywhere between a simmer and a rolling boil. It also provides control of temperature in accordance with a temperature setting by the operator. The microcontroller 22 may be embodied by a microprocessor known to one of ordinary skill in the art comprising a processor, read-only memory (ROM), random access memory (RAM) and input-output ports. Although the illustrative embodiment of system 10 shown in FIG. 1 shows a heat generator 25 having a gas energy source for use in a gas cooking appliance 48 (FIG. 2A), the invention may be carried out with other types of heat generators 25, such as those employing quartz halogen, microwave or inductively coupled energy.

Referring now to FIGS. 2A–2D, FIG. 2A shows a pictorial view of a gas cooking appliance 48 which incorporates system 10 for providing autonomous control of the cooking process atop the gas appliance 48. The cooktop of appliance 48 has four burners 29 with a vessel 11 positioned on one of the burners 29. Such an appliance may have one or more burners 29 with automatic control of the heating process. FIGS. 2B–2D are exploded views showing in FIG. 2B the digital display 24 having a representative temperature reading of 237° F. and showing the inclusion of the microcontroller 22 in the gas cooking appliance 48. FIG. 2C shows the temperature sensor 12 located in the center of the burner 29, and FIG. 2D shows the operator interface 16 which the operator sets to a specific temperature or to a simmer or boil position depending on a desired mode of operation. The use of the invention in a gas cooking appliance 48 works with standard cookware, covered or uncovered, is non-intrusive because nothing is put into the food or pot, vessel or pan, works at any altitude and any use environment, and provides rapid heat-up to boiling without burning or overshoot.

There are two distinct temperature control modes when the thermal process is used for cooking as follows:

(1) In order to hold the liquid simmering without a boil-over, detection of (incipient) boiling is required and the heat input reduced to let simmering continue. Here, the boiling process itself provides an upper limit to the temperature, and control of the heat input rate is needed to keep the vessel from boiling over.

(2) In order to hold the temperature of the vessel 11 fixed at a value below the incipient boiling temperature of a heterogenous liquid component, when that temperature is approached from below, the microcontroller 22 simply reduces the average heat enough to hold the temperature fixed within an allowed band.

In either case, the desired temperature may be approached rapidly, but at a rate which avoids scorching or burning.

Referring now to FIG. 3, a pictorial view of the cooking vessel 11 of FIG. 2 shows the center point 46 on the bottom of the vessel 11 where temperature is measured by the temperature sensor 12. Also illustrated is a circular zone 47 around the center point 46 where the gas flame 32 applies heat input (H) 67 to the vessel 11.

Figure 8A:
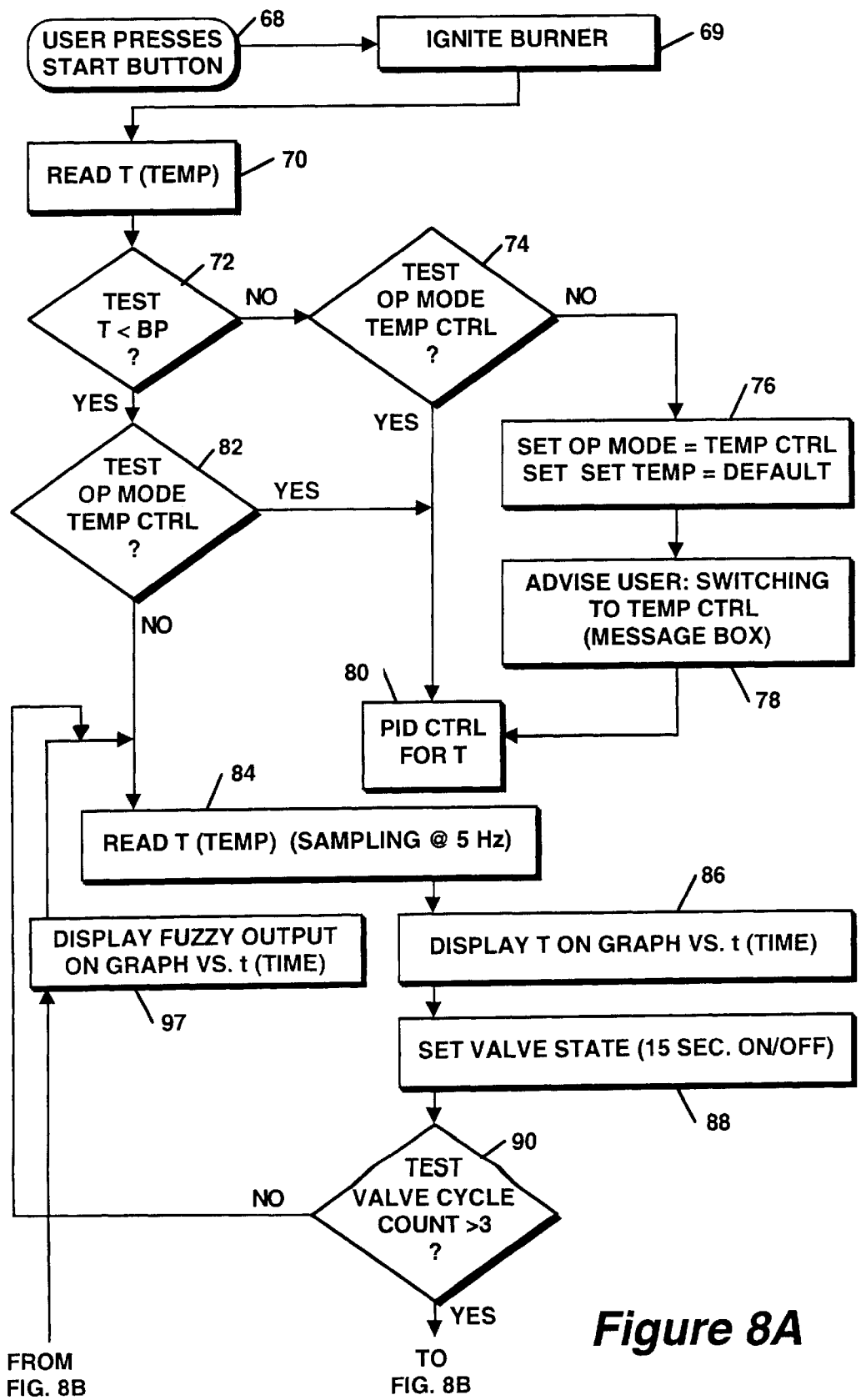
FIGS. 8A and 8B show a flow chart of a control supervisor program in a microcontroller for controlling a simmer or boil control mode of operation and a temperature control mode of operation.
Figure 8B:
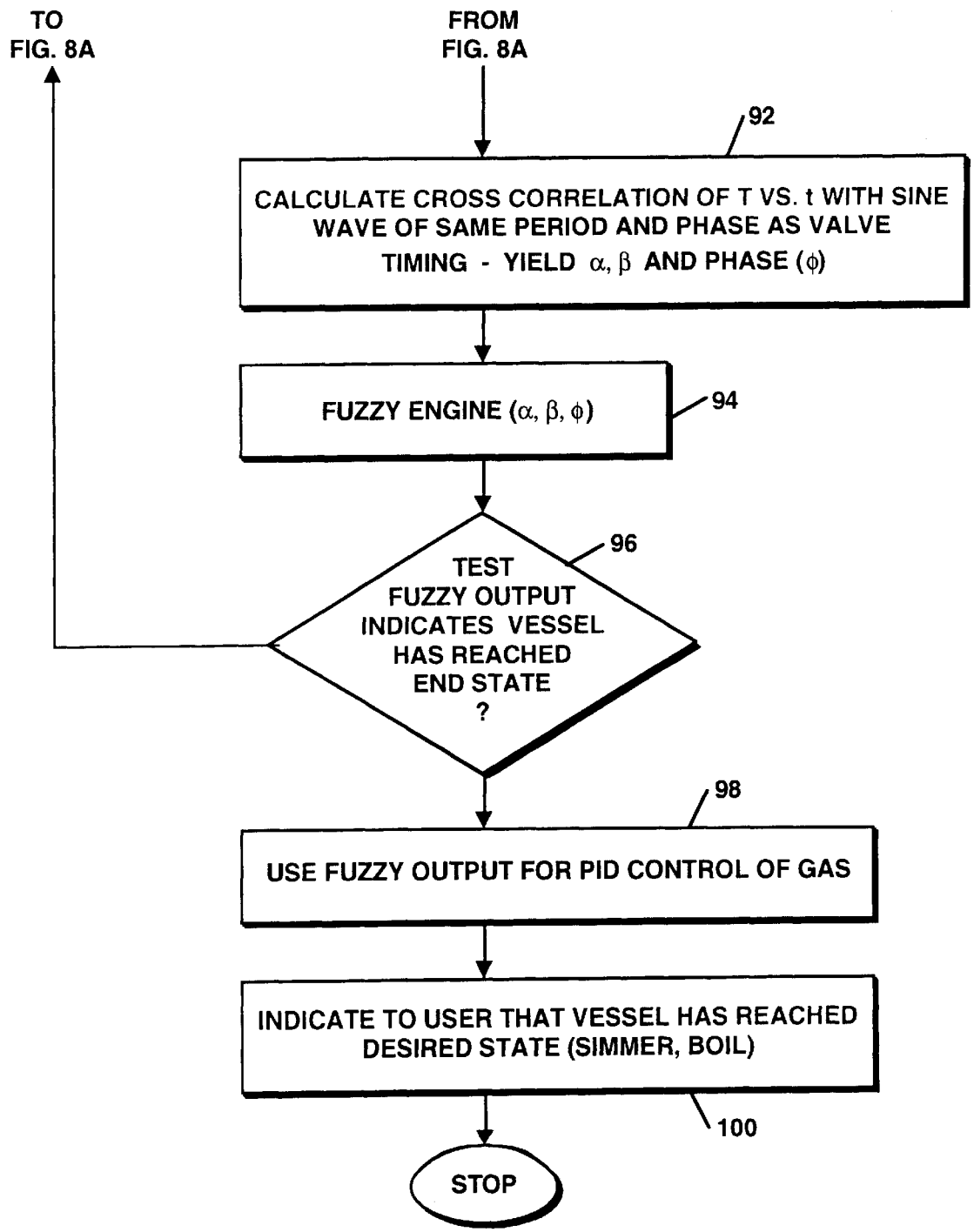

Referring now to FIG. 4, the microcontroller 22 comprises a control supervisor 50 program for controlling a set simmer or set boil mode of operation (Mode I) and a set temperature mode of operation (Mode II). A flow chart of the control supervisor is shown in FIGS. 8A and 8B and described hereinafter. The control supervisor 50 interfaces with and controls a parameter calculator 52, a fuzzy logic analyzer 54, a proportional/integral/derivative (PID) control algorithm 56 device for Mode I operation and a PID control algorithm 58 device for Mode II operation. It also interfaces with operator interface 16 output signals both digital and analog (via the A/D converter 18). The parameter calculator 52 receives temperature (T) data from the A/D converter 18 and vessel sensor (VS) data and generates key parameters ($\alpha$, $\beta$ and $\phi$) in real time based on the temperature expression $T(t)=\alpha t+\beta \sin((2\pi/P)t+\phi)$ from which the onset of boiling can be determined and controlled. The parameters $\phi$, $\beta$ and $\phi$, which are further described below, are fed to the fuzzy logic analyzer 54 along with heat input (H) and time (t) data, and in accordance with predetermined rules set up in the fuzzy logic analyzer 54, a boil state 55 signal is generated which indicates the boiling point of a liquid and it is fed to PID control algorithm 56. The output of the PID control algorithm 56 is fed to a heat control generator 60 which provides the heat modulation control 40 signal to the gas valve digital controller 28. When the system 10 is operating in Mode II or the set temperature mode, the temperature (T) data is fed directly to PID control algorithm 58 and the output of PID control algorithm 58 is fed to the heat control generator 60 which generates the heat modulation control 40 signal. The heat control generator 60 also provides the spark control 42 signal which ignites the gas to form the flame 32 which provides the heat (H) input to the process. The PID control algorithm 56 and PID control algorithm 58 are known to one of ordinary skill in the art. They are controllers that use proportional integral and derivative functions. The integral function automatically raises the stabilized system temperature to match the set point temperature to eliminate the difference caused by the proportional function. The derivative function monitors the rate of rise or fall of the system temperature and automatically adjusts the output of the PID control algorithm to minimize overshoot or undershoot.

For temperature control (Mode II), the heat control generator 60 interprets the PID control algorithm 58 analog signal and sends the heat modulation control 40 digital signal to the gas valve digital controller 28 for providing the proper amount of heat. For simmer/boil control (Mode I), the heat control interprets the PID control algorithm 56 analog signal and sends alternating high and low heat signals, the average of which provides the proper amount of heat and the cycling of which provides the information needed for the parameter calculator 52. The heat control generator 60 also activates spark control 42 signal whenever gas valve 30 is open. The sparking is suppressed when a flame 32 is detected.

Figure 5:
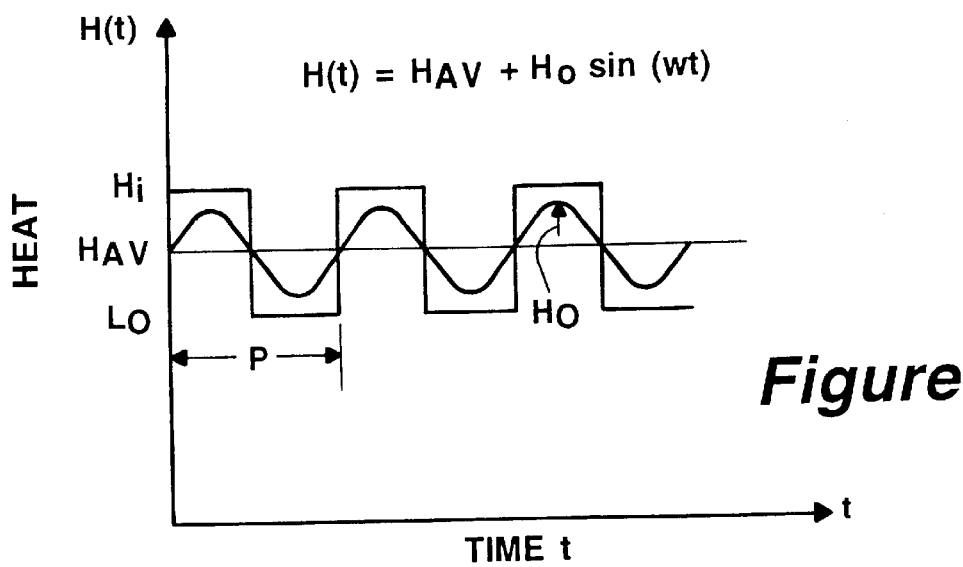
FIG. 5 is a graph showing heat (H(t)) being periodically switched from a low to a high to a low level for controlling the temperature in a vessel.
Figure 6A:
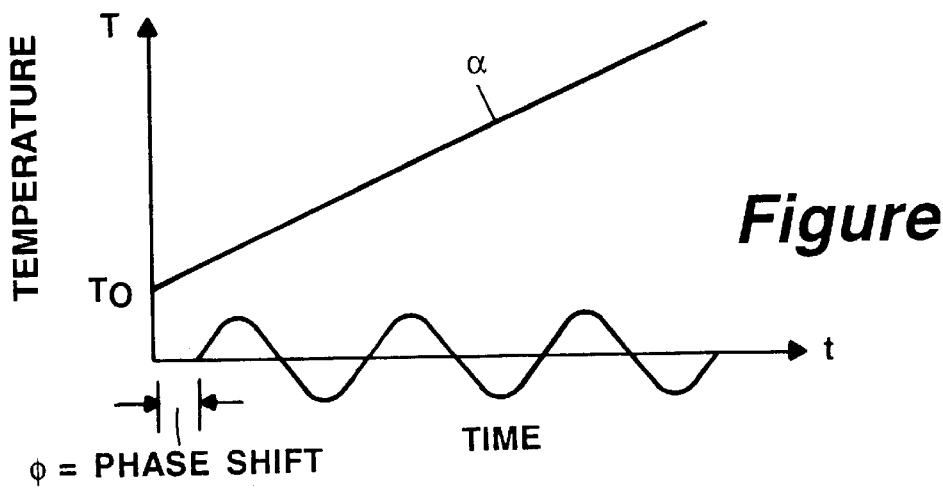
FIG. 6A is a graph showing a phase shift ($\phi$) that occurs in the temperature (T(t)) reading at the vessel after heat (H(t)) being applied to the vessel is increased or decreased, and showing the average rate of change of temperature ($\alpha$) due to the periodic application of heat.

Referring now to FIG. 5 and FIG. 6A, FIG. 5 is a graph showing heat (H(t)) being periodically switched as a function of time from a low level to a high level to a low level for controlling the temperature in the vessel 11. The expression for H(t) is as follows:

$$H(t) = H_{AV} + H_o \sin(\omega t)$$

where, $H_{AV}$=average heat $H_O$=amplitude of modulated heat

FIG. 6A is a graph showing the phase shift $\phi$ parameter or shift in the time of the temperature response T(t) relative to the heat input H(t) of FIG. 5, and the linear heating is represented by the slope $\alpha$ of the time-temperature curve. In the illustrative embodiment of FIG. 1, phase sensitive detection is applied to process control in cooking. Phase sensitive detection involves using an exciting signal (the heat modulated control 40 signal) that is periodic in time. The system 10 response as expressed by T(t) is then detected in lock-step with the exciting signal.

Figure 6B:
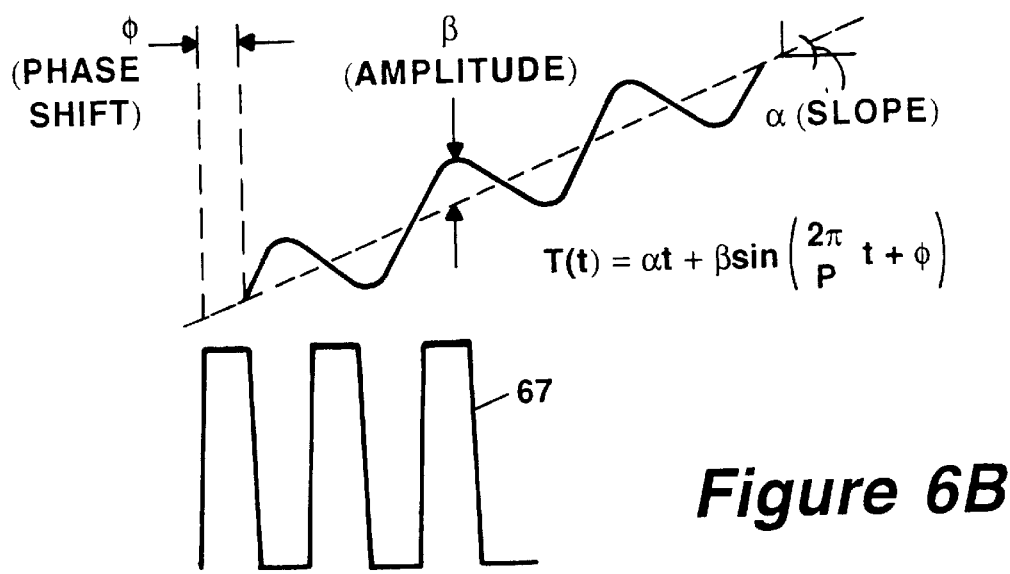
FIG. 6B is a graph showing the combined effect on temperature of the linear and modulated heating and defining the key parameters $\alpha$, $\beta$ and $\phi$.

Referring now to FIG. 6B, a graph is shown of the combined effect on temperature of the linear and modulated heating components. The temperature T(t) is described by the following equation which comprises the key parameters of slope ($\alpha$), modulation amplitude ($\beta$), and phase shift ($\phi$):

$$T(t) = \alpha t + \beta \sin\left(\frac{2\pi}{P} + \phi\right)$$

The linear heating is represented by term a which is the slope of the time-temperature curve. The temperature response to modulated heating is represented by the term $$\beta \sin\left(\frac{2\pi}{P} + \phi\right)$$

As shown in FIG. 6B, $\beta$ is the amplitude of the periodictemperature waveform resulting from the modulated heat input 67 and $\phi$ is the phase shift measured from the leading edge of the modulated heat input 67 to the leading edge of the temperature response to such heat input 67 as illustrated in FIG. 6B.

The description of the invention at this point requires some background in the thermodynamics of a container of liquid exposed to a heat source. Considering a semi-infinite solid with its surface temperature varying as a sinusoidal function of time, the differential equation describing the temperature of a point in the bulk is:

$$\frac{\partial^2 T}{\partial x^2} = \frac{1}{k} \frac{\partial T}{\partial t} \tag{1}$$

Here, T is the temperature and k is the thermal diffusivity, given by $$k = \frac{K}{cd} \tag{2}$$

where K is the thermal conductivity, c is the specific heat, and d is the mass density of the material. Both the liquid and the container must be considered.

The diffusivity is a measure of how far the heat flows in unit time. One can estimate X, the "distance traversed" in time t, using the rule $$X = \sqrt{kt} \tag{3}$$

Assuming the temperature at the y-z plane located at x=0 is given as a boundary condition by $$T(t) = A\cos(\omega t) \tag{4}$$

where $\omega$ is the angular frequency measured in radians/second. The solution of the PDE given in Equation 1 that obeys the above boundary condition given in Equation 4 is $$T(t) = Ae^{-px}\cos(\omega t - px) \tag{5}$$

where p is given by $$p = \sqrt{\frac{\omega}{2k}} \tag{6}$$

The wavelength of the temperature wave propagating into the bulk is $$\lambda = \frac{1}{p} = \sqrt{\frac{2k}{\omega}} \tag{7}$$

For a given frequency $\omega$, the wavelength increases with the square root of diffusivity. One can determine the diffusivity of a liquid by heating a vessel uniformly over a large area in the middle of its bottom and performing one of several temperature measurements (along the axis of the vessel at distance x from the bottom):

1. the decay of the amplitude of the temperature wave along the axis, using Equations 5 and 6;
2. the relative phase shift at distance x and using $\Delta\phi = x\sqrt{(\omega/2k)}$;
3. the propagation velocity of temperature changes into the liquid and using $v = \omega/p = \sqrt{(2k\omega)}$.

Knowing the diffusivity of a liquid allows selection of an average heat rate such that uniform heating can take place. Low diffusivity liquids are generally more difficult to heat evenly and are prone to local overheating (i.e., burning or sticking on the bottom or boiling over). With a single temperature transducer in the center of a burner, the second method above for measuring diffusivity can be used; the phase relationship between a step change in heat input and the temperature rise at the transducer carries information about diffusivity. Naturally, the vessel itself conducts heat, which can mask the contribution of the liquid contents to the temperature response phase shift. Thin vessels with low horizontal heat conducting will work best with this technique. Thermally massive pots and low liquid volumes will make accurate estimation of liquid diffusivity difficult.

Boiling point detection is straightforward and relies on the principle that the apparent specific heat of a liquid becomes infinite when the liquid reaches its boiling point; the temperature of a liquid cannot be raised above its boiling point. It might be possible simply to monitor the temperature of a liquid while it is heated, looking for the point at which the temperature ceases to rise. If, however, the heat input is low enough that the vessel reaches its steady state (heat input equaling heat loss) before the liquid reaches a boil, the temperature curve will flatten, leading to a false detection of boiling. The solution is to pulse the heat input; step changes in heat input cause increases in the temperature rate of rise until the liquid reaches its boiling point. At or near the boiling point, a step in the heat input will cause a small or negligible change in the liquid temperature rate of rise.

Figure 7:
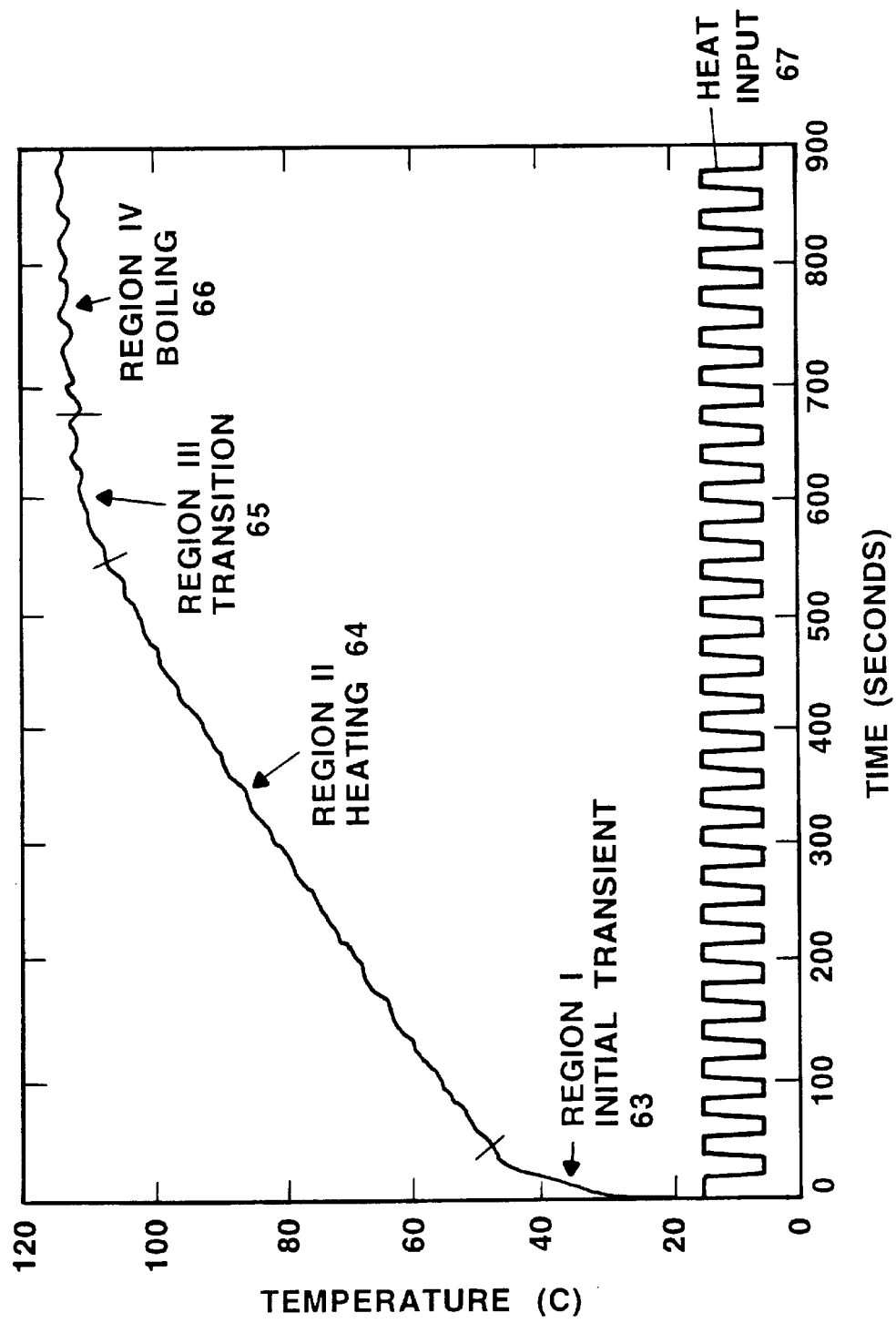
FIG. 7 is a graph showing a time-temperature response of a vessel containing a liquid and having modulated heat applied to the vessel until a boiling point is reached.

Referring now to FIG. 7, a representative graph of the time-temperature T(t) response of a vessel 11 containing a liquid and having modulated heat H(t) applied to the vessel until a boiling point is reached is shown. The square wave below the time temperature curve represents high/low pulsations for the gas and the flame 32 producing the modulated heat input 67 to the vessel 11 and liquid therein. In response to the fluctuating component of the heat input 67, FIG. 7 shows that the temperature increases not just steadily but with small periodic excursions added on a steady growth trend. It is the phase relationship of the excursions to the cycling of the gas valve 30 and the excursions' amplitude relative to the depth of the gas modulation that gives this invention the required resolution to see through the chaotic fluctuations of the cooking processes.

Still referring to FIG. 7, four regions of the process are shown as follows:

Region I is the initial transient 65 region and has the steepest slopes. It is the initial heating where the vessel absorbs heat and passes little heat to the contents.

Region II is the heating 64 region where the vessel content is being heated but it is below the boiling point. The heating region has a slope of approximately one. This region is affected by many factors, including the diffusivity, specific heat and mass of the contents and the vessel.

Region III is the transition 65 region between a slope of one and zero and is the region of incipient boiling.

Region IV is the boiling 66 region. It is the flat part of the curve effectively pinning the maximum temperature. Additional heat input 67 cannot increase the content's temperature.

Referring now to FIGS. 8A and 8B, a flow chart is shown of the control supervisor 50 program in the microcontroller 22. The program starts when a user presses a start button 68 and a burner 29 ignites 69; this is followed by performing a Read T(temp) 70 and a test 72 is made to determine if temperature (T) is sufficiently less than the boiling point of the liquid. In this embodiment, 90° C. (10° C. below the boiling point of water (100° C.)) is the target threshold temperature ($T_{THRESHOLD}$) If the temperature is greater than the $T_{THRESHOLD}$, then a test 74 is made to determine if the temperature control operational mode (Mode II) was selected. If it was selected, then the temperature reading of step 70 is fed to the PID control algorithm 58 for monitoring and controlling 80 the temperature. If the temperature mode was not selected, then the operational mode is forced to temperature control (Mode II) and the temperature reading 70 is fed to the PID control algorithm 58 for controlling 80 temperature. Referring again to test 72, if the temperature is less than $T_{THRESHOLD}$, then test 82 is performed; if the temperature control operational mode was selected, then the temperature reading of step 70 is fed to the PID control algorithm 58 for controlling 80 the temperature. If test 82 determines that the temperature control (MODE II) is not selected, then the program proceeds to perform a simmer or boil mode of operation (Mode I).

Still referring to FIGS. 8A and 8B, the set simmer or set boil mode of operation proceeds by sampling the temperature readings every 200 ms (5 HZ rate) 84 and displays the temperature (T) on a graph of T vs time (t) 86. In the next step 88 the gas valve 30 state is varied every 15 seconds from high flow to low flow and then back to high flow. Next, a test 90 is performed whereby the gas valve 30 is cycled three times. Until three cycles have occurred, the program goes back to read the temperature at step 84 based on the sampling rate of 5 Hz. At the end of three gas valve 30 cycles a calculation 92 is performed of the cross correlation of T vs t with a sine wave of the same period as the valve cycles which produces the parameters $\alpha$, $\beta$ and $\phi$. This is done by the parameter calculator 52 in the microcontroller 22. The calculated parameters $\alpha$, $\beta$ and $\phi$ are then used by the fuzzy logic analyzer 54 or fuzzy engine to determine an end state, and test 96 is performed by the fuzzy engine output to determine when the end state or boiling point is reached. Until this end state is reached, the fuzzy engine output is displayed in step 97 on a graph. As long as the fuzzy engine output does not indicate a boiling point has been reached, the program continues to cycle taking temperature readings at step 84 and calculating new values for parameters $\alpha$, $\beta$ and $\phi$ over three cycles of the gas valve 30 every 200 ms sample. When the fuzzy engine output indicates that the vessel contents has reached its end state or boiling point at test 96, then a boil state 55 signal is fed to PID control algorithm 56 which generates a signal for the heat control generator 60 in order to control in step 98 the gas and hence the heat input to the vessel 11. In the next step 100 the digital display 24 indicates to a user that the vessel has reached the desired state of simmer or boil.

Referring again to FIG. 4, the parameter calculator 52 receives the temperature (T) data and generates the key parameters $\alpha$, $\beta$ and $\phi$ in real time. The temperature (T) is sampled every 200 ms and the periodic heat input 67 has a cycle period of 30 seconds, 15 seconds high flow and 15 seconds low flow. The parameter calculator 52 performs the real time cross-correlation function every 200 ms commencing with the third cycle of the heat input H(t). The 30 second cycle period and the 200 ms sampling rate which are used for the preferred embodiment may be varied for other applications. These values for the various parameters are chosen as examples and they have been used in the present embodiment.

The real time cross-correlation of the temperature (T) data with a control voltage (heat modulation control 40) is calculated by parameter calculator 52. A cross-correlation peak happens when the phase shift $\phi$ is equal to the phase angle between the periodic heat input H(t) and the periodic temperature response T(t). The value of this peak is a direct measure of the temperature fluctuation due to the periodic application of heat H(t). As data taking starts, immediately after the initial transition which gives an indication of the type of vessel 11 and amount of thermal mass in communication with the temperature sensor 12, the average linear slope $\alpha$ of the steadily increasing trend of the temperature data is calculated. Soon thereafter, the cross-correlation produces the amplitude $\beta$ of the temperature fluctuations.

The parameter calculator 52 comprises a software routine, that is readily implemented by one of ordinary skill in the art, which continuously solves the following equations for the required parameters α, β and φ:

$$\text{CROSS CORRELATION: } h(t, t_0) = \int_{t}^{t+3P} dx f(x)g(x+t_0)$$

$$\text{AVERAGE TEMPERATURE SLOPE: } \alpha = \left\langle \frac{dT}{dt} \right\rangle$$

$$\text{TEMPERATURE: } T(t) = \alpha t + \beta \sin(\omega t + \phi)$$

Figure 9:
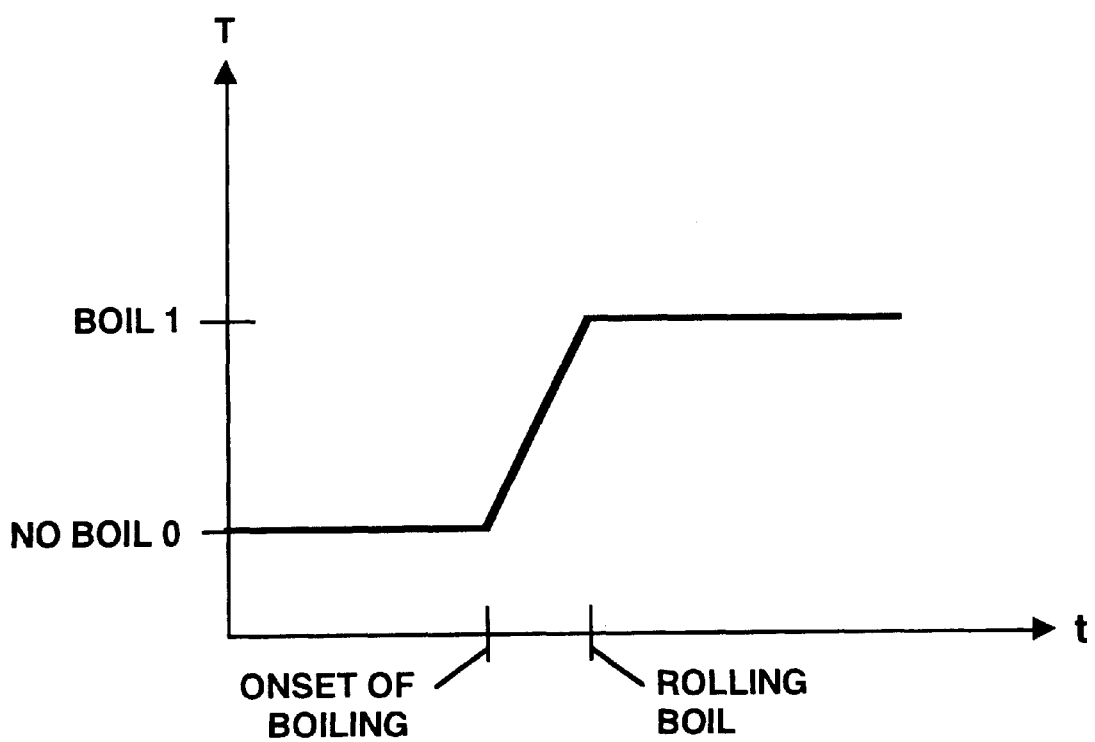
FIG. 9 is a graph illustrating the output signal from the fuzzy logic analyzer as a liquid reaches its boiling point.

Still referring to FIG. 4 and also referring to FIG. 9, the fuzzy logic analyzer 54 comprises a fuzzy logic software package which may be embodied by the Model MatLab® Fuzzy Toolbox, and manufactured by MathWorks, Inc., of Natick, Mass. It comprises a learning algorithm which is trained, preconditioned or programmed by empirically obtained data. Although fuzzy logic is the preferred supervisory control method, other more direct supervisory control methods known in the art may be feasible. Data are collected for a variety of different types of cooking vessels 11 such as heavy aluminum, steel, stainless steel, copper clad, thin aluminum and cast iron, each having contained therein various liquids such as water, milk, and spaghetti sauce and varying amounts of such liquids. Time (t), temperature (T) and heat input (H) are recorded on a computer disk of a commonly available personal computer at a 5 Hz rate or every 200 ms as heat is applied to the vessel. At each data point reading an operator watching the heating process enters a zero or a one for each data point, where an entered zero indicates the liquid is not boiling and an entered one indicates the liquid is boiling as shown in FIG. 9. The time-temperature data of the empirical data stored on the disk is fed to the parameter calculator 52 for calculating α, β and φ and these parameters along with heat and the boiling state are fed to the fuzzy logic analyzer 54 of FIG. 4 with the fuzzy logic software operating in a preconditioning or training mode. As a result of this training or refinement of the logic rules in the fuzzy logic software, the fuzzy logic analyzer 54 is able to make a boiling state decision remarkably close to the boiling state data observed by an operator.

Figure 10:
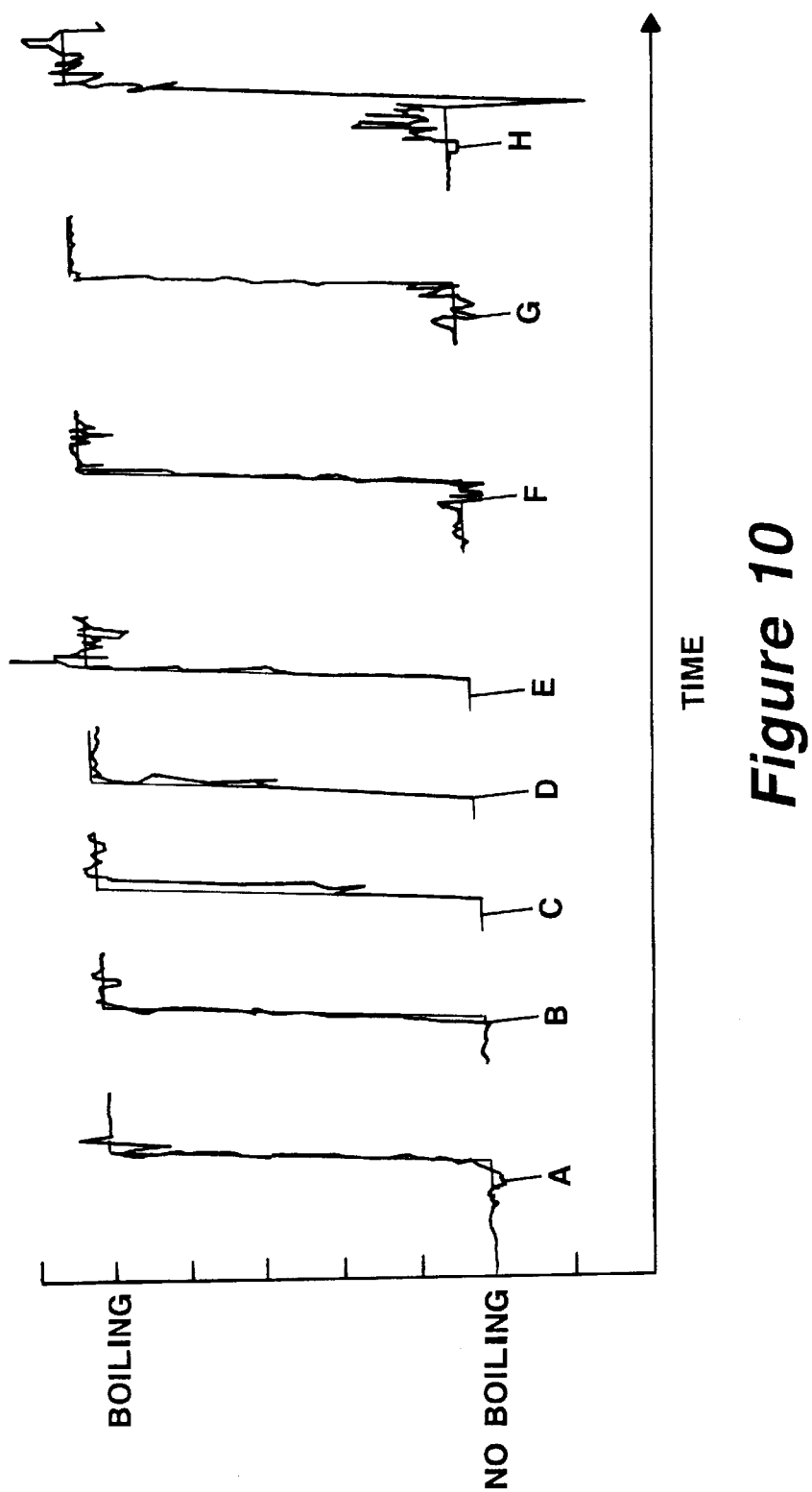
FIG. 10 is a graph showing a series of output responses from a predetermined fuzzy logic analyzer superimposed on ideal outputs as shown in FIG. 9 obtained by an operator observing a liquid entering a boiling state.

Referring now to FIG. 9 and FIG. 10, a series of output responses from the trained fuzzy logic analyzer 54 are graphically shown in FIG. 10 superimposed on ideal outputs such as shown in FIG. 9 obtained by an operator observing various liquids as each liquid approaches the onset of boiling and then enters the boiling state. The responses shown in FIG. 10 are for the types of vessels and liquids as follows:

| RESPONSE | VESSEL | LIQUID | VOLUME |
| --- | --- | --- | --- |
| A | Heavy Aluminum | water | 800 ml |
| B | Heavy Aluminum | water | 400 ml |
| C | Heavy Aluminum | water | 200 ml |
| D | Heavy Aluminum | Spaghetti Sauce | 200 ml |
| E | Heavy Aluminum | Milk | 200 ml |
| F | Thin Aluminum | Water | 800 ml |
| G | Copper/Stainless | Water | 800 ml |
| H | Cast Iron | Water | 800 ml |

This invention has been disclosed in terms of certain embodiments. It will be apparent that many modifications can be made to the disclosed apparatus without departing from the invention. For example, the boiling point of many industrial liquids may be detected and controlled by the present invention thereby providing a plurality of applications for the invention. In addition, other heat generator energy sources besides gas may be used to provide the modulated heat input. Therefore, it is the intent of the appended claims to cover all such variations and modifications as come within the true spirit and scope of this invention.

What is claimed as new and desired to be secured by Letters Patent of the United States is:

1. In a system for monitoring and controlling the state of a thermal process, the improvement comprising:
   means for providing a fluctuating heat input to a container in response to a heat control signal;
   means for sensing temperature of said container;
   means connected to said temperature sensing means for calculating parameters based on fluctuations of temperature at said container, said parameters including a linear rate of change (α) of said temperature, an amplitude (β) of said temperature fluctuations in response to said fluctuating heat input, and a phase shift (φ) of said temperature fluctuations relative to said fluctuating heat input;
   fuzzy logic means, having inputs connected to said α, β, and φ outputs of said parameter calculating means and said heat control signal for generating a signal indicating a boiling point of said liquid; and
   means connected to an output of said fuzzy logic means for generating said heat control signal.

2. The system as recited in claim 1 wherein said container comprises a metal, said metal comprises aluminum, copper, steel, stainless steel, cast iron or combinations thereof.

3. The system as recited in claim 1 wherein said means for providing said fluctuating heat input comprises a gas valve controller means for controlling a gas flame.

4. The system as recited in claim 1 wherein said temperature sensing means comprises a resistance temperature device.

5. The system as recited in claim 1 wherein said temperature sensing means comprises a thermocouple.

6. The system as recited in claim 1 wherein said temperature sensing means comprises an infrared sensor.

7. The system as recited in claim 1 wherein said calculating parameter means comprises solving a time-temperature equation $T(t)=\alpha t+\beta \sin(\omega t+\phi)$.

8. The system as recited in claim 1 wherein said fuzzy logic means comprises logic rules which are preconditioned with empirical boiling point data for a plurality of types of liquids and containers prior to said fuzzy logic means being used in said system.

9. The system as recited in claim 1 wherein said means for generating said heat control signal comprises:
   proportional/integral/derivative control algorithm means connected to said fuzzy logic means output for generating a response based on detecting said boiling point; and
   heat control means coupled to an output of said proportional/integral/derivative control algorithm means for generating said heat control signal.

10. The system as recited in claim 1 wherein said system comprises means coupled to said temperature sensing means for supervising said monitoring and controlling of said thermal process including said calculating parameter means, said fuzzy logic means and said heat control signal generating means.

11. The system as recited in claim 10 wherein said supervising means includes a microcontroller means for controlling functions of said thermal process.

12. The system as recited in claim 10 wherein said system comprises:

operator interface means for setting a temperature at said container;

said supervising means includes a set temperature monitor means connected to an output of said temperature sensing means for comparing said set temperature to said temperature from said temperature sensing means; and said means for generating said heat control signal, connected to an output of said temperature monitoring means, adjusts said control signal to provide said heat input to said container enabling said temperature of said container to equal said set temperature.

13. In a cooking appliance for heating a liquid in a vessel, the improvement comprising:

means for setting a mode of operation for detecting and controlling a boiling point of said liquid;

means for providing a heat input to said vessel in response to a heat control signal, said heat input including a fluctuating heat input;

means positioned within said heat input providing means for sensing temperature of said vessel;

means connected to said temperature sensing means for calculating parameters based on fluctuations of temperature at said vessel, said parameters including a linear rate of change ($\alpha$) of said temperature, an amplitude ($\beta$) of said temperature fluctuations in response to said fluctuating heat input, and a phase shift ($\phi$) of said temperature fluctuations relative to said fluctuating heat input;

fuzzy logic means, having inputs connected to said $\alpha$, $\beta$, and $\phi$ outputs of said parameter calculating means and said heat control signal, for generating a signal indicating a boiling point of said liquid;

means connected to an output of said fuzzy logic means for generating said heat control signal, said heat control signal maintaining said liquid temperature in accordance with said preset mode of operation; and means coupled to said temperature sensing means for supervising said mode of operation including said calculating parameter means, said fuzzy logic means and said heat control signal generating means.

14. The cooking appliance as recited in claim 13 wherein said heating input providing means comprises a gas burner.

15. The cooking appliance as recited in claim 13 wherein said appliance comprises a plurality of heat input providing means, each of said heat input providing means being controlled in accordance with a preselected mode of operation.

16. The cooking appliance as recited in claim 13 wherein said vessel comprises a metal, said metal comprises aluminum, copper, steel, stainless steel, cast iron or combinations thereof.

17. The cooking appliance as recited in claim 13 wherein said means for providing said fluctuating heat input comprises a gas valve controller means for controlling a gas flame.

18. The cooking appliance as recited in claim 13 wherein said temperature sensing means comprises a resistance temperature device.

19. The cooking appliance as recited in claim 13 wherein said temperature sensing means comprises a thermocouple.

20. The cooking appliance as recited in claim 13 wherein said temperature sensing means comprises an infrared sensor.

21. The cooking appliance as recited in claim 13 wherein said calculating parameter means comprises solving a time-temperature equation $T(t)=\alpha t+\beta \sin(\omega t+\phi)$.

22. The cooking appliance as recited in claim 13 wherein said fuzzy logic means comprises logic rules which are preconditioned with empirical boiling point data for a plurality of types of liquids and vessels prior to said fuzzy logic means being used in said system.

23. The cooking appliance as recited in claim 13 wherein said means for generating said heat control signal comprises:

proportional/integral/derivative control algorithm means connected to said fuzzy logic means output for generating a response based on detecting said boiling point; and heat control means coupled to an output of said proportional/integral/derivative control algorithm means for generating said heat control signal.

24. The cooking appliance as recited in claim 13 wherein said mode of operation includes a preset simmer mode and a preset boil mode, each mode being maintained by controlling said temperature of said liquid.

25. The cooking appliance as recited in claim 13 wherein said means for setting a mode of operation further comprises:

means for setting a temperature at said vessel;

said supervising means includes a set temperature monitor means connected to an output of said temperature sensing means for comparing said set temperature to said temperature from said temperature sensing means; and said means for generating said heat control signal, connected to an output of said temperature monitoring means, adjusts said control signal to provide said heat input to said vessel enabling said temperature of said vessel to equal said set temperature.

26. The cooking appliance as recited in claim 13 wherein said appliance comprises a display means coupled to said supervising means for displaying information.

27. The cooking appliance as recited in claim 13 wherein said supervising means comprises a microcontroller means for controlling functions of said set mode of operation.

28. The cooking appliance as recited in claim 13 wherein said temperature sensing means comprises an analog to digital converter means for converting temperature data and operator interface data to digital signals.

29. The cooking appliance as recited in claim 23 wherein said heat control means comprises means for generating a signal for controlling a spark generator.

30. The cooking appliance as recited in claim 13 wherein:

said heat input means includes means for sensing a vessel in contact with said heat input means.

31. In a method for monitoring and controlling the state of a thermal process in a container holding a liquid, an improvement comprising the steps of:

providing a fluctuating heat input to said container in response to a heat control signal;

sensing temperature of said container with temperature sensing means;

calculating parameters based on fluctuations of temperature at said container provided by said temperature sensing means, said parameters including a linear rate of change ($\alpha$) of said temperature, an amplitude ($\beta$) of said temperature fluctuations in response to said fluctuating heat input, and a phase shift ($\phi$) of said temperature fluctuations relative to said fluctuating heat input;

generating a signal indicating a boiling point of said liquid with fuzzy logic means, having inputs connected to said α, β, and φ outputs of said parameter calculating means and said heat control signal; and generating said heat control signal with means connected to an output of said fuzzy logic means.

32. The method as recited in claim 31 wherein said method includes the step of providing said container comprising a metal, said metal comprises aluminum, copper, steel, stainless steel, cast iron or combinations thereof.

33. The method as recited in claim 31 wherein said step of providing a fluctuating heat input comprises the step of using a gas valve controller means for controlling a gas flame.

34. The method as recited in claim 31 wherein said step of sensing said temperature of said container comprises the step of using a resistance temperature device.

35. The method as recited in claim 31 wherein said step of sensing temperature of said container comprises the step of using a thermocouple.

36. The method as recited in claim 31 wherein said step of sensing temperature of said container comprises the step of using an infrared sensor.

37. The method as recited in claim 31 wherein said step of calculating parameters comprises the step of solving a time-temperature equation $T(t)=\alpha t+\beta \sin(\omega t+\phi)$.

38. The method as recited in claim 31 wherein said step of generating a signal indicating a boiling point of said liquid with fuzzy logic means comprises the step of preconditioning logic rules of said fuzzy logic means with empirical boiling point data for a plurality of types of liquids and containers prior to said fuzzy logic means being used in said system for detecting said boiling point.

39. The method as recited in claim 31 wherein said step of generating said heat control signal comprises the steps of:

providing a proportional/integral/derivative control algorithm means connected to an output of said fuzzy logic means for generating a response based on detecting said boiling point; and generating said heat control signal with heat control means connected to said response of said proportional/integral/derivative control algorithm means.

40. In a method for heating a liquid in a vessel on a cooking appliance, an improvement comprising the steps of:

setting a mode of operation for detecting and controlling a boiling point of said liquid;

providing a heat input to said vessel in response to a heat control signal, said heat input including a fluctuating heat input;

sensing temperature of said vessel with temperature sensing means positioned within said heat input providing means;

calculating parameters based on fluctuations of temperature at said vessel provided by said temperature sensing means, said parameters including a linear rate of change (α) of said temperature, an amplitude (β) of said temperature fluctuations in response to said fluctuating heat input, and a phase shift (φ) of said temperature fluctuations relative to said fluctuating heat input;

generating a signal indicating a boiling point of said liquid with fuzzy logic means connected to said α, β, and φ outputs of said parameter calculating means and said heat control signal;

generating said heat control signal with means connected to an output of said fuzzy logic means, said heat control signal maintaining said liquid temperature in accordance with said preset mode of operation; and supervising said mode of operation including said calculating parameter means, said fuzzy logic means and said heat control signal generating means with means coupled to said temperature sensing means.

41. The method as recited in claim 40 wherein said step of providing said heat input comprises the step of using a gas burner.

42. The method as recited in claim 40 wherein said method comprises the step of providing a plurality of heat input providing means, each of said heat input providing means being controlled in accordance with a preselected mode of operation selected.

43. The method as recited in claim 40 wherein said method includes the step of providing said vessel comprising a metal, said metal comprises aluminum, copper, steel, stainless steel, cast iron or combinations thereof.

44. The method as recited in claim 40 wherein said step of providing said fluctuating heat input comprises the step of providing a gas valve controller means for controlling a gas flame.

45. The method as recited in claim 40 wherein said step of sensing temperature comprises the step of using a resistance temperature device.

46. The method as recited in claim 40 wherein said step of sensing temperature comprises the step of using a thermocouple.

47. The method as recited in claim 40 wherein said step of sensing temperature comprises the step of using an infrared sensor.

48. The method as recited in claim 40 wherein said step of calculating parameters comprises the step of solving a time-temperature equation $T(t)=\alpha t+\beta \sin(\omega t+\phi)$.

49. The method as recited in claim 40 wherein said step of detecting a boiling point with fuzzy logic means comprises the step of preconditioning logic rules of said fuzzy logic means with empirical boiling point data for a plurality of types of liquids and vessels prior to said fuzzy logic means being used in said appliance for detecting said boiling point.

50. The method as recited in claim 40 wherein said step of generating said heat control signal comprises the steps of:

providing a proportional/integral/derivative control algorithm means connected to an input of said fuzzy logic means output for generating a response based on detecting said boiling point; and generating said heat control signal with heat control means coupled to an output of said proportional/integral/derivative control algorithm means.

51. The method as recited in claim 40 wherein said step of setting a mode of operation comprises the step of setting a simmer mode or a boil mode, each mode being maintained by controlling said temperature of said liquid.

52. The method as recited in claim 40 wherein said step of setting a mode of operation further comprises the steps of:

setting a temperature to occur at said vessel;

comparing said set temperature to said temperature from said temperature sensing means in said supervising means; and adjusting said heat control signal to provide said heat input to said vessel enabling said temperature of said vessel to equal said set temperature.

53. The method as recited in claim 40 wherein said appliance method comprises the step of displaying information in accordance with a display means coupled to said supervising means.

54. The method as recited in claim 40 wherein said step of supervising said mode of operation comprises the step of providing a microcontroller means for controlling functions of said set mode of operation.

55. The method as recited in claim 40 wherein said step of sensing temperature comprises the step of converting temperature data and operator interface data from analog to digital signals.

56. The method as recited in claim 50 wherein said step of generating said heat control signal comprises the step of generating a signal for controlling a spark generator for a gas flame with said heat control means.

57. The method as recited in claim 40 wherein:

said step of providing a heat input to said vessel comprises the step of sensing a vessel in contact with said heat input providing means.

\* \* \* \* \*